United States Patent
Peters et al.

(10) Patent No.: US 6,858,738 B2
(45) Date of Patent: Feb. 22, 2005

(54) PROCESS FOR MAKING AMLODIPINE, DERIVATIVES THEREOF, AND PRECURSORS THEREFOR

(75) Inventors: Theodorus H. A. Peters, Arnhem (NL); Franciscus B. G. Benneker, Rheden (NL); Pavel Slanina, Lelekovice (CZ); Jiri Bartl, Strelice (CZ)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 10/431,536

(22) Filed: May 8, 2003

(65) Prior Publication Data

US 2003/0220501 A1 Nov. 27, 2003

Related U.S. Application Data

(60) Division of application No. 09/938,840, filed on Aug. 27, 2001, now Pat. No. 6,653,481, which is a continuation-in-part of application No. 09/809,351, filed on Mar. 16, 2001, now abandoned.
(60) Provisional application No. 60/258,613, filed on Dec. 29, 2000.

(51) Int. Cl.[7] ............................................. C07D 209/48
(52) U.S. Cl. ...................................................... 548/479
(58) Field of Search ........................................ 548/479

(56) References Cited

U.S. PATENT DOCUMENTS

| | | | |
|---|---|---|---|
| 4,572,909 A | 2/1986 | Campbell et al. | |
| 4,818,766 A | 4/1989 | Ostermayer et al. | |
| 4,879,303 A | 11/1989 | Davison et al. | |
| 4,983,740 A | 1/1991 | Peglion et al. | |

(List continued on next page.)

FOREIGN PATENT DOCUMENTS

| | | |
|---|---|---|
| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| EP | 1266654 A1 | 12/2002 |
| EP | 1287826 | 3/2003 |
| JP | 002677 | 1/2001 |
| RU | 2161156 | * 12/2000 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long–acting dihydropyridine calcium antagonists. 9. Structure activity relationships around amlodipine," Eur J Med Chem (1991) 26, 907–913.

(List continued on next page.)

Primary Examiner—Patricia L. Morris
(74) Attorney, Agent, or Firm—Mark R. Buscher

(57) ABSTRACT

Amlodipine and related analogues thereof are prepared by the following general reaction scheme:

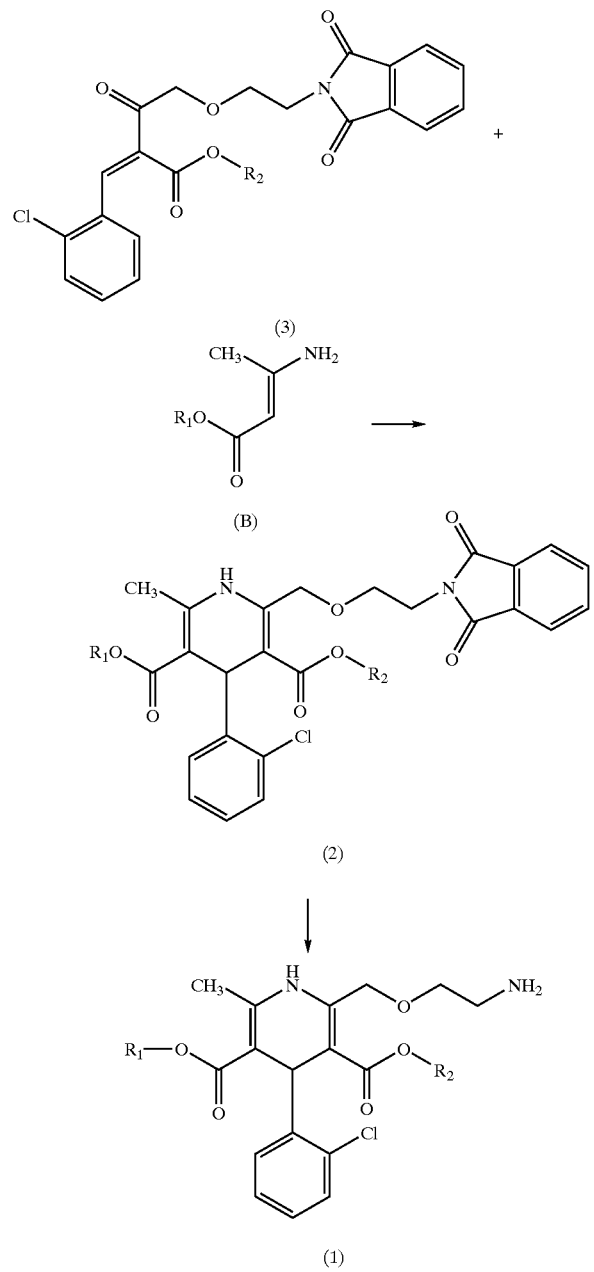

$R_1$ and $R_2$ each independently represent a $C_1$–$C_4$ alkyl group. The process provides for the formation of compounds of formula (1) in good yield and purity. Further, the compounds of formula (1) can be used as calcium channel blockers or as reference standards or reference markers for checking the purity of amlodipine.

8 Claims, No Drawings

U.S. PATENT DOCUMENTS

| | | | |
|---|---|---|---|
| 5,155,120 | A | 10/1992 | Lazar et al. |
| 5,389,654 | A | 2/1995 | Furlan et al. |
| 5,424,321 | A | 6/1995 | Hellberg et al. |
| 5,438,145 | A | 8/1995 | Furlan et al. |
| 6,046,337 | A | 4/2000 | Bozsing et al. |
| 6,479,525 | B2 | 11/2002 | Lemmens et al. |
| 6,518,288 | B2 | 2/2003 | Lemmens et al. |
| 6,538,012 | B2 | 3/2003 | Ettema |
| 6,600,047 | B2 | 7/2003 | Benneker et al. |
| 6,602,893 | B2 | 8/2003 | Lemmens et al. |

OTHER PUBLICATIONS

Amlodipine Besylate Monograph, PHARMEUROPA vol. 10, No. 2, 197–198, Jun. 1998.

Faulkner et al., "Absorption of Amlodipine Unaffected by Food," Arzneim Forsch/Drug Res. 39 (11), No. 7, (1989).

McDaid and Deasy, "Formulation development of transdermal drug delivery system for amlodipine base," International Journal of Pharmaceutics 133 (1996) 71–83.

Arrowsmith et al., "Long–Acting Dihydropyridine Calcium Antagonists. 1.2–Alkoxymethyl Derivatives Incorporating Basic Substitutents," J. Med. Chem. American Chemical Society, 1986, 29, 1696–1702.

FDA FOIA Material on Amlodipine Besylate, NDA No. 19–787, "Review of an Original NDA," Oct. 10, 1990.

\* cited by examiner

PROCESS FOR MAKING AMLODIPINE, DERIVATIVES THEREOF, AND PRECURSORS THEREFOR

This application is a divisional application under 35 U.S.C. § 121 of prior application Ser. No. 09/938,840, filed Aug. 27, 2001 now U.S. Pat. No. 6,653,481, which is a continuation in part under 35 U.S.C. § 120 of prior U.S. application Ser. No. 09/809,351, filed Mar. 16, 2001 now abandoned, both of which claim the benefit of priority under 35 U.S.C. § 119(e) from provisional patent application Ser. No. 60/258,613, filed Dec. 29, 2000. The entire contents of application Ser. Nos. 09/938,840 and 09/809,351 are incorporated herein by reference.

BACKGROUND OF THE INVENTION

1. Field of the Invention

The present invention relates to novel intermediates useful in the synthesis of amlodipine and related compounds as well as to processes of making and using the same.

2. Description of the Related Arts

EP 89167 and corresponding U.S. Pat. No. 4,572,909 describe a class of dihydropyridine derivatives that exhibit antianginal and antihypertensive properties. One of the compounds disclosed therein has become a commercially important compound that is now known as amlodipine: or 2-[(2-aminoethoxy)methyl]-4-(2-chlorophenyl)-1,4-dihydro-6-methyl-3,5-pyridinedicarboxylic acid 3-ethyl 5-methyl ester, having the following formula:

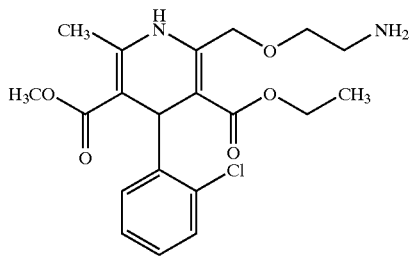

This compound, in the form of its besylate salt as described in EP 244 944 and in corresponding U.S. Pat. No. 4,879,303, is the active ingredient in the prescription pharmaceutical composition NORVASC sold by Pfizer Pharmaceuticals for management of hypertension and angina pectoris.

Generally, the synthetic route disclosed in EP 89167 for making amlodipine and the other related dihydropyridine compounds comprises forming the corresponding amino-group protected precursor followed by deprotection. Suitable protecting groups for the amino side chain group include benzylamino, dibenzylamino, azido and phthalimido groups. One of the precursors for amlodipine uses a phthalimido protecting group and is represented by the following formula (2a).

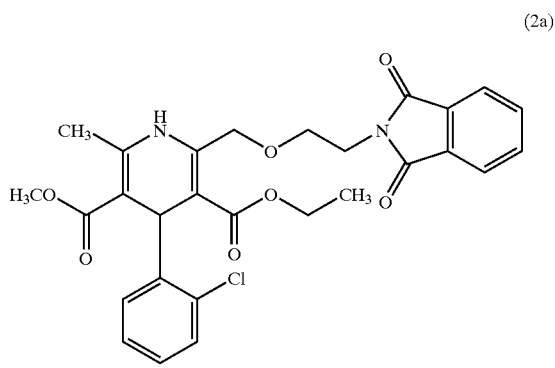

This compound, which is hereinafter referred to as "phthalimidoamlodipine," has certain advantages among other amino-protected precursors for amlodipine as it may be easily separated from the reaction mixture without danger (e.g. the azido-amlodipine is explosive) and is converted to amlodipine by simple, common deprotection procedures, e.g. by reaction with methylamine, hydrazine etc. It is thus considered to be a particularly useful key intermediate for industrial production of amlodipine.

J. Med. Chem. 1986, 29, 1696–1702 discloses two routes for making the phthalimidoamlodipine and other related amino-protected precursors. The first route comprises reacting a substituted benzaldehyde (A), such as 2-chlorobenzaldehyde, with methyl 3-aminocrotonate (B1) and amino protected aminoethoxy-methylacetoacetate (C1').

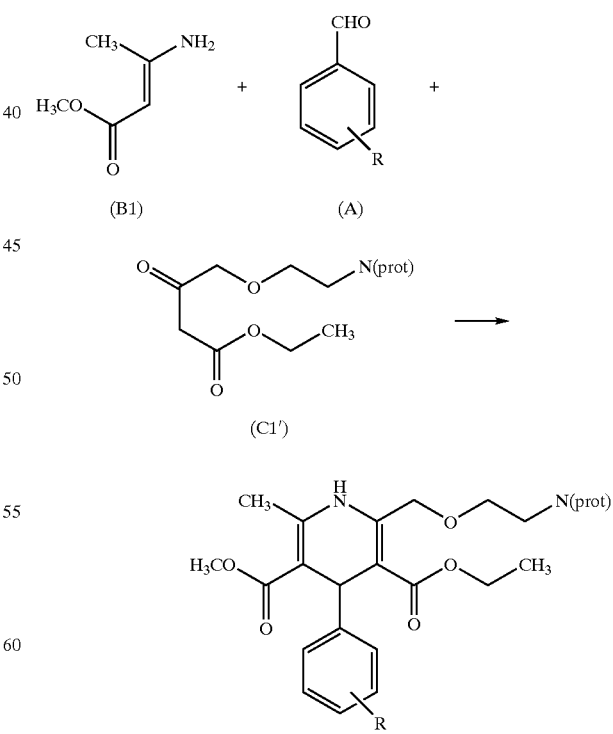

The compound (C1') is prepared by a condensation of ethyl 2-chloroacetoacetate (shown hereinafter as compound (F)) with an appropriately substituted sodium alkoxide. Where —N(prot) represents a phthalimido-group, the alkoxide can be N-(2-hydroxyethyl)phthalimide (shown hereinafter as compound G).

The second route disclosed in this article, comprises reacting a benzylidene derivative (D1) (prepared in an extra step by an addition of a compound of formula (A), such as o-chlorobenzaldehyde, to methyl acetoacetate) with a substituted aminocrotonate (E1) (prepared in situ from the above amino-protected aminoethoxymethylacetoacetate (C1') and ammonium acetate).

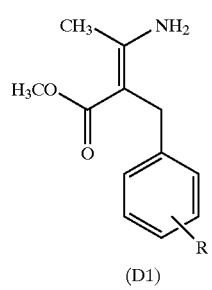

(D1)

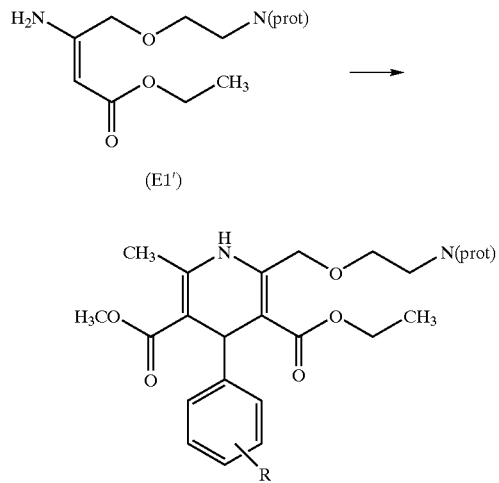

(E1')

This variant was also applied to the synthesis of phthalimidoamlodipine (2a) in WO 00-24714. Therein, the intermediating phthalimido-substituted aminocrotonate (E1) was not prepared in situ but was prepared and isolated in a solid state in an extra step prior to the reaction with the benzylidene compound.

The above methods suffer from yield and/or purity inefficiencies due to the reactivity of starting materials leading to formation of side products. For example, phthalimidoamlodipine is reported in the above-mentioned J. Med. Chem. Article as being prepared in 25% yield by following the first scheme (see compound 41 in Table I on page 1698). It would be desirable to provide a process for making phthalimidoamlodipine and related compounds in good yield and with good purity.

SUMMARY OF THE INVENTION

It has now been discovered that phthalimidoamlodipine (2a) as well as related phthalimido-protected precursors can be prepared by a convenient method, with a good yield and purity, by employing a new starting material. Accordingly, a first aspect of the invention relates to a compound having the formula (3):

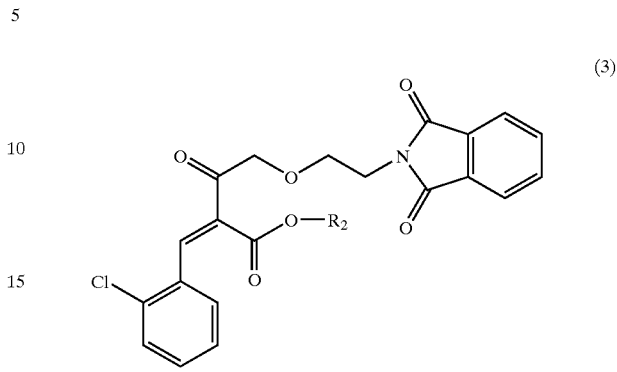

Wherein $R_2$ represents a $C_1$–$C_4$ alkyl group, preferably an ethyl group. The compounds of formula (3) can be reacted with an alkyl 3-aminocrotonate of formula (B) to form a phthalimido-protected precursor of formula (2) as shown below:

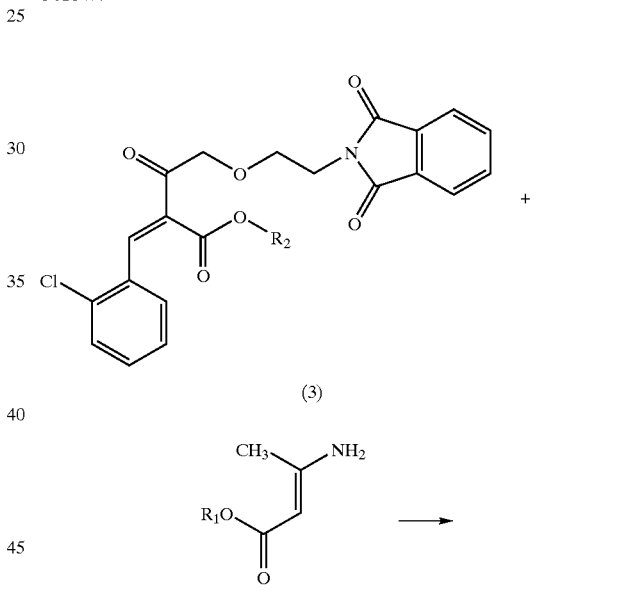

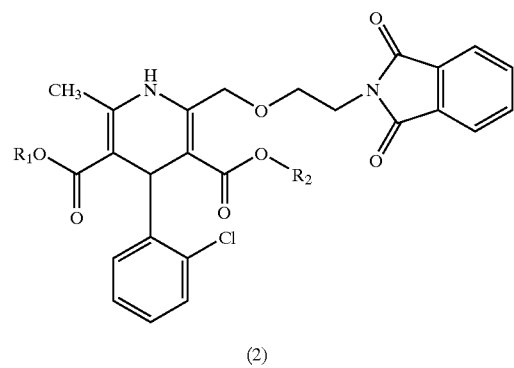

(2)

wherein $R_1$ and $R_2$ each independently represent a $C_1$–$C_4$ alkyl group. The compounds of formula (2) can be deprotected to form compounds of formula (1):

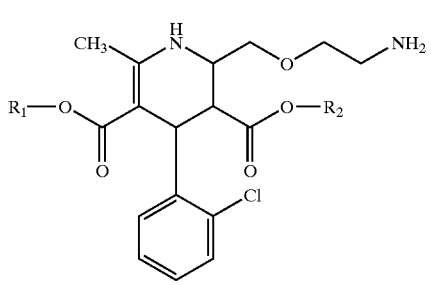

(1)

Preferably $R_1$ is methyl and $R_2$ is ethyl whereby the process forms amlodipine via the phthalimidoamlodipine (2a). The other compounds of formula (1) are also useful as calcium channel blockers for treating angina or hypertension. Additionally, these compounds and the corresponding phthalimido-protected precursors of formula (2) are useful as reference standards or markers for checking the respective purity of amlodipine or phthalimidoamlodipine, a salt thereof, or a composition containing the same; i.e. assaying for these formula (1) compounds which can be formed as side-products in commercial manufacture of amlodipine via transesterification for example.

DETAILED DESCRIPTION OF THE INVENTION

The present invention deals with new compounds, alkyl 2-(o-chlorobenzylidene)-4-(2-phthalimidoethoxy) acetoacetates of formula (3)

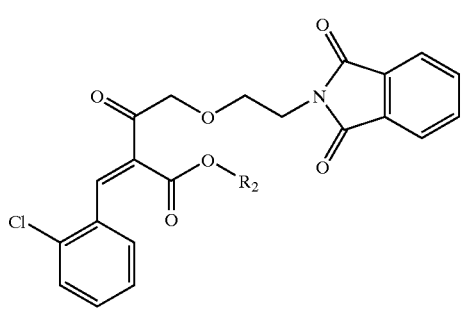

(3)

wherein $R_2$ represents a $C_1$–$C_4$ alkyl group and it preferably represents an ethyl group (compound 3a), a methyl group (compound 3b) or an isopropyl group (compound 3c).

The compound (3) may be prepared in a sufficiently pure state and simply isolated from a crude reaction mixture by any conventional techniques. Such an isolated form of the compound (3) can be further purified if needed or used directly in the next synthetic step. Due to the presence of a carbon-carbon double bond in the molecule, the compound (3) may be prepared as a mixture of cis- and trans- isomers or as a single cis- or trans isomer. The formation of a trans-isomer is driven thermodynamically (trans-isomer is preferably formed at elevated temperatures), while the formation of cis-isomer is driven kinetically. From the use aspects, the compound (3) in a form of a mixture of cis-and trans isomers is preferred; however, single isomers are also within the scope of the invention.

Among the compounds of general formula (3), the compound (3a) is particularly important as it represents an industrially applicable intermediate in the synthesis of amlodipine.

The present invention also provides a process for providing the compound of formula (3), comprising reacting o-chlorobenzaldehyde with alkyl 4-(2-(phthalimido)ethoxy) acetoacetate of formula (C).

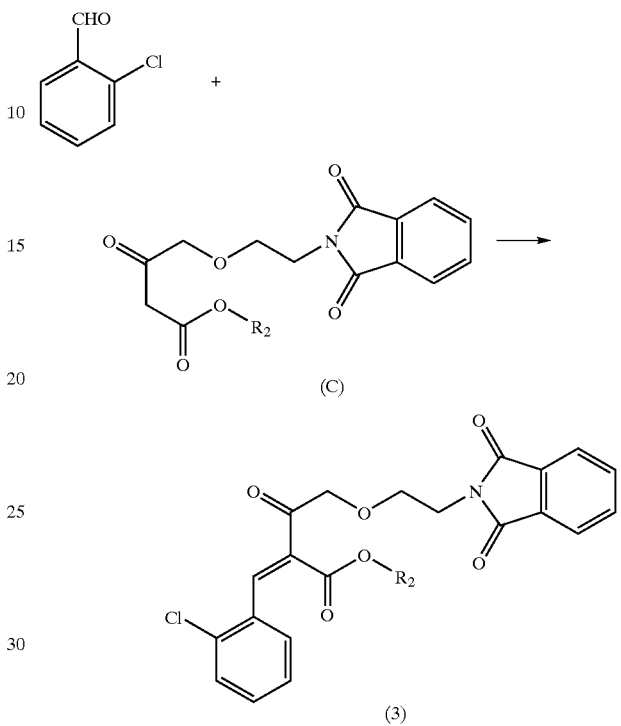

Typically the reaction is carried out in a reaction solvent, preferably an organic solvent such as an alcohol, especially isopropanol or in a hydrocarbon such as benzene, advantageously in a presence of an organic base such as piperidine or piperidine acetate. The solvent should be one in which the compound (3) product is only sparingly soluble, so that it may be separated from the rest of the unreacted starting materials and also from any potential side products. The reaction may be performed at temperatures from close to ambient up to the boiling point of the solvent, usually about 20 to 55° C., preferably at 20–40° C. Water formed by the reaction may be separated out e.g. by azeotropic distillation though this is not required.

If the reaction is performed in isopropanol, the product (3) separates out in an oily state. Preferably the compound (3) oil is recovered and used directly without further purification to form phthalimidoamlodipine as such oil contains only minor amounts of impurities and the remaining starting materials can be easily removed. Recovery can be by any known technique and is typically accomplished by a liquid-liquid phase separation optionally with washing of the oil product. It should be understood that such washing is not intended to be considered a "purification step", but rather merely part of the recovery. Thus, it is an advantage of this process that although the disadvantages of an "in-situ" production of (3) are avoided, the isolation and purification of the intermediate (3) is not necessary.

In a preferred embodiment, the process provides the compound (3a) as outlined below.

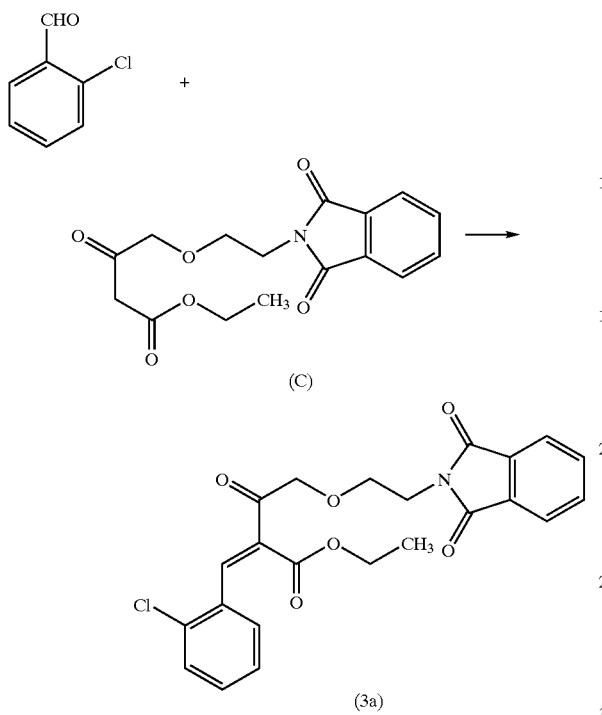

The usual ratio of cis- and trans isomers of the compound (3) formed in the process of our invention is from about 7:3 to about 5:5, respectively. For example, compounds (3a) and (3c) are usually formed in a cis:trans ratio of about 6:4 while the compound (3b) is usually formed at about a 1:1 ratio of cis:trans.

Another possibility for preparing the compounds of formula (3) could be by reacting o-chlorobenzaldehyde with an alkyl 2-chloroacetylacetoacetate (F), such as ethyl 2-chloroacetylacetoacetate (F1), under general conditions described in EP 212340, to form a benzylidene-2-chloroacetylacetoacetate intermediate of formula (4). The compound (4) is reacted with N-(2-hydroxyethyl) phthalimide (G) to form the compound (3). The process is outlined in the following scheme with regard to forming compound (3a).

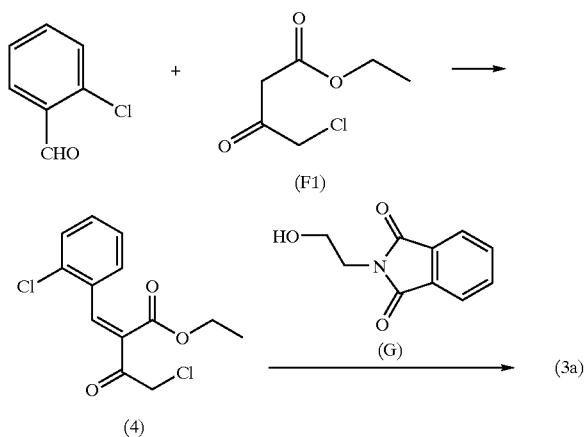

All of the starting materials for the above-described reaction schemes, e.g. compounds of formula (C), (F), etc., are either commercially available or readily obtained by workers of ordinary skill by methods sufficiently described in the prior art.

The compounds of formula (3) can be used to produce a phthalimido-protected precursor of formula (2) by reacting the same with an alkyl 3-aminocrotonate of formula (B) as shown below.

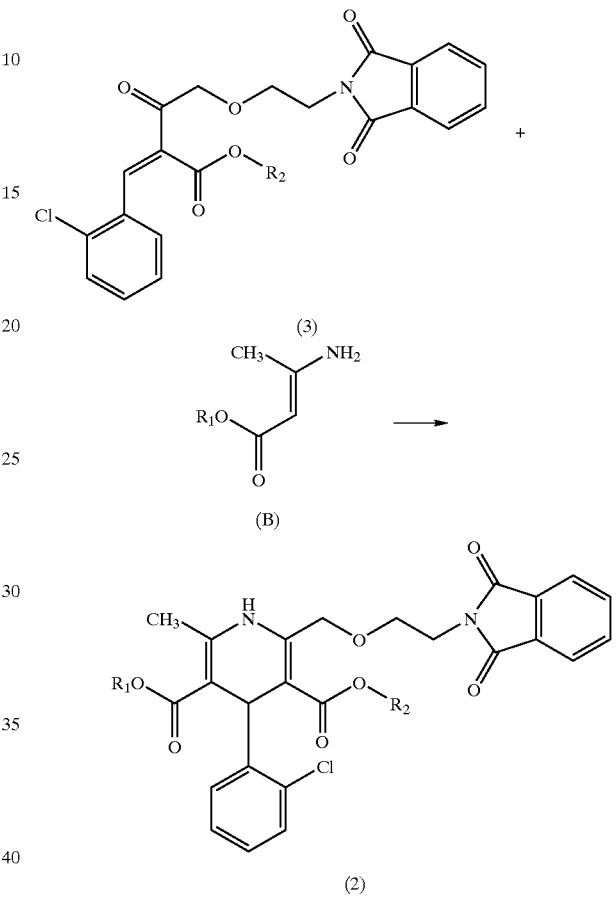

$R_1$ and $R_2$ each independently represent a $C_1$–$C_4$ alkyl group. The reaction between (3) and (B) may preferably be performed in a suitable solvent, e.g. in isopropanol, at elevated temperatures, advantageously at 70–90° C., as the reaction is thermally driven. The speed of reaction may be enhanced by the addition of a catalytic amount of a strong acid and/or by addition of a dehydrating agent, e.g., a molecular sieve, for trapping the formed water. After the reaction, the product (2) may be isolated in a solid state after cooling the reaction mixture and/or after concentration of the reaction mixture. If desired, the product (2) can be purified by recrystallization from a solvent such as methanol, ethanol, 2-propanol, ethyl acetate, etc. or a mixture of two more of such solvents. After a single recrystallization, e.g. from ethyl acetate, the product typically exhibits a purity higher than 98%.

Thus, in summary, the use of the compound (3) of our invention in the synthesis of phthalimidoamlodipine (2a) and other related phthalimido-protected precursors avoids the disadvantages of both disclosed synthetic variants of the prior art. In respect to the variant 1, it allows for a reduction in side products by producing a stable intermediate that is easily separable from the rest of the reactive starting materials, thereby reducing the chance of side effects in subsequent reaction steps. In respect to variant 2, it does not require an extra step of conversion of a keto group to an amino group which decreases the overall yield of the process and further it does not require an isolation of the intermediate in a crystalline state. Further, the fact that the chlorobenzaldehyde is reacted in a separate step so that the unreacted portion may be absent from the final cyclization reaction is advantageous in both the yield and purity of the compounds of formula (2).

The compounds of formula (2) can be subjected to a deprotecting step to form a compound of formula (1).

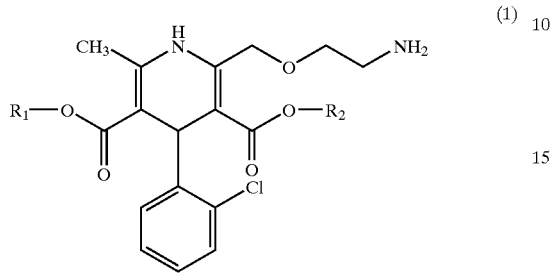

(1)

Again $R_1$ and $R_2$ each independently represent a $C_1$–$C_4$ alkyl group. Phthalimidoamlodipine and other compounds of formula (2) may be converted to amlodipine and corresponding analogues as represented by formula (1) by any of the conventional methods of deprotection of the phthalimido group such as those disclosed in EP 89167. Examples of deprotecting agents include ethanolic methylamine, hydrazine hydrate or alkali metal hydroxide/acid treatment. Particularly preferred however is a variant of the first method that employs commercially available aqueous solution of methylamine. The reaction with aqueous methylamine may be performed at a temperature from the ambient to approx. 60° C., preferably at 25–40° C. In a preferred embodiment, amlodipine free base is subsequently separated out from the concurrently produced methylphthalimide by an extraction of the aqueous reaction mixture with a water immiscible organic solvent, e.g. by toluene, and, optionally, is isolated from the solution in that solvent.

Amlodipine as well as all the compounds of formula (1) may be isolated as a free base and/or it may be converted into an acid addition salt by a reaction of the base with the corresponding acid. Alternatively, acid addition salts of amlodipine and of other compounds of formula (1) may be prepared without isolating the corresponding free base. For instance, a solution of amlodipine free base obtained from the step of deprotection of phthalimidoamlodipine may be used as well. The solution of crude base, without need of isolation of such free base, is contacted with corresponding acid, and the formed salt is separated from the solution.

Suitable acid addition salts include pharmaceutically acceptable acid addition salts of amlodipine such as amlodipine besylate, hydrochloride, frumarate, maleate and mesylate, including solvates and hydrates thereof. Particularly suitable are amlodipine maleate and amlodipine mesylate monohydrate.

The compounds of formula (1) can be formulated into a pharmaceutical composition comprising an effective amount of amlodipine or a pharmaceutically acceptable salt thereof and at least one pharmaceutically acceptable excipient. Generally the pharmaceutical composition is in the form of a unit dose having from 1 to 25 mg of the compound of formula (1), measured as the free base. This usually provides a dose sufficient to treat or prevent angina or hypertension. Suitable dosage forms include oral solid dosage forms such as tablets and capsules or liquid forms such as for oral or parenteral administration. The compositions can be made by known techniques such as wet or dry granulation techniques including direct compression tabletting.

Additionally, the compounds of formula (1) can also be used as reference standards or markers for checking the purity of amlodipine. Particularly useful are the analogues of amlodipine of the formulae (1b), (1c), (1d), (1e) and (1f).

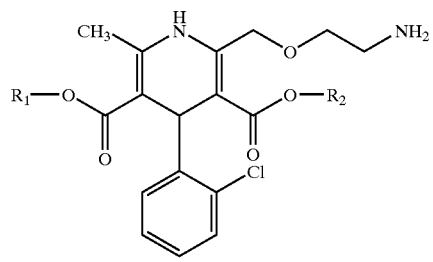

1b): $R_1$=ethyl, $R_2$=ethyl
1c): $R_1$=methyl, $R_2$=methyl
1d): $R_1$=ethyl, $R_2$=methyl
1e): $R_1$=prop-2-yl, $R_2$=ethyl
1f): $R_1$=methyl, $R_2$=prop-2-yl The compounds (1b)–(1f) are important side products/impurities which may appear in the industrial production of amlodipine, especially when an alcohol solvent is employed. That is, the compounds of formula (2) and formula (1) can undergo transesterification such that $R_1$ or $R_2$ or both are changed from one alkyl group to another. Thus, the following compounds (2b)–(2f) may also arise during the production of amlodipine from the phthalimidoamlodipine precursor and are also useful as markers or reference standards for monitoring purity.

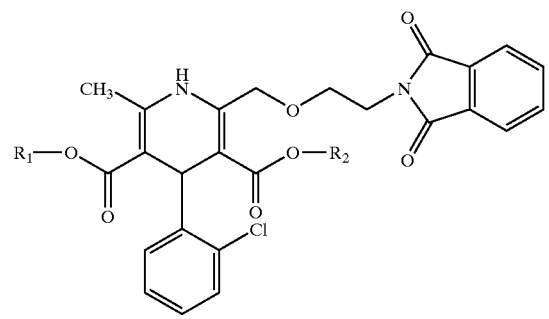

2a): $R_1$=methyl, $R_2$=ethyl
2b): $R_1$=ethyl, $R_2$=ethyl
2c): $R_1$=methyl, $R_2$=methyl
2d): $R_1$=ethyl, $R_2$=methyl
2e): $R_1$=prop-2-yl, $R_2$=ethyl
2f): $R_1$=methyl, $R_2$=prop-2-yl When present as an unintended transesterification impurity/side-product, the compounds (2b)–(2f) will also convert into their corresponding compound (1b)–(1f) during the deprotection step. Alternatively, during the deprotection step or any later processing step, the compounds of formula (1) can also undergo transesterification thereby changing the alkyl group in one or both of the $R_1$ and $R_2$ positions. Transesterification can occur unintentionally during the production of amlodipine, either by the present process or the prior methods, where an alcohol solvent such as ethanol, isopropanol, etc. is used. Transesterification reactions may appear in whatever production step in the production of phthalimidoamlodipine, so that a producer should appreciate to have a method by which the amounts of such undesired products could be monitored.

Fortunately, the process of the present invention allows for the formation of the compounds (1b)–(1f) and (2b)–(2f) in a sufficiently pure state so as to be suitable for use as a reference standard or marker in detecting the presence of these potential impurities in the amlodipine, its salts, its precursors, and its compositions including pharmaceutical compositions, and in the phthalimidoamlodipine, its salts, and its compositions, respectively.

In detail, compounds (2b)–(2f) are preparable in an essentially pure state by following the process of the invention as described above. Alternatively, the compounds of formula (2) may be subjected to a (deliberate) transesterification reaction to provide other compounds of the same general formula (2), however bearing other groups $R_1$, $R_2$. An example of this process is set forth hereinafter for the synthesis of (2e).

To obtain the compound (2b), the compound (3a) of our invention reacts with ethyl 3-aminocrotonate (compound (B2)). To obtain the compound (2c), the compound (3b) reacts with methyl 3-amino crotonate (B1) to yield the desired product (2c). The compound (3b) can be prepared, inter alia, by condensation of o-chlorobenzaldehyde with methyl 4-(2-(phthalimido)ethoxy)acetoacetate (compound C2). Compound C2 can be prepared by a prior art procedure as described above for compound C1'.

To obtain the compound (2d), compound (3b) reacts with ethyl 3-aminocrotonate (B2) in analogy with the above.

Synthesis of the compound (2f) starts from the isopropyl-analogue of compound (3a), i.e. from compound (3c). The compound (3c) can be prepared by both the processes of the present invention outlined above, advantageously by condensation of o-chlorobenzaldehyde with isopropyl 4-(2-(phthalimido)ethoxy)acetoacetate (compound C3). Compound C3 can be prepared by a prior art procedure as described above for compound C1'. The prepared compound (3c) reacts with methyl 3-amino crotonate (B1) to yield the desired product (2f) under basically same conditions as outlined above.

To obtain the compound (2e), phthalimidoamlodipine (2a) is transesterified by heating in isopropanol under catalysis of a strong acid, e.g. sulfuric acid.

Amlodipine analogues (1b)–(1f) may be obtained from corresponding phthalimidoamlodipine analogues (2b)–(2f) under reaction conditions as known and/or as described above for the synthesis of amlodipine. Accordingly, compounds (1b)–(1f) may be purified to a desired degree of purity by conventional purification methods and/or may be converted into conventional acid addition salts and optionally purified. Alternatively, the compounds (1b)–(1f) can be prepared by subjecting amlodipine to a (deliberate) transesterification reaction.

The process of testing of purity of products comprising amlodipine ("amlodipine products") or phthalimidoamlodipine advantageously comprises, in essence, any technique that can resolve or otherwise detect the presence of the target compound. Examples of this type of assay include thin layer chromatography (TLC) and high performance liquid chromatography (HPLC).

The amlodipine product to be assayed for the presence of any one or more of potential amlodipine impurities (1b)–(1f) is any product that comprises amlodipine free base or any acid addition salt of amlodipine. Examples of the amlodipine product include the reaction mixture obtained after deprotection of phthalimidoamlodipine, crude amlodipine free base recovered during synthesis, purified amlodipine free base, reaction mixture obtained in the production of acid addition salts of amlodipine, crude acid addition salt of amlodipine or purified acid addition salt of amlodipine of any suitable form including crystalline forms or amorphous forms, and pharmaceutical unit dosage forms containing the same. Acid addition salt of amlodipine means any acid addition salt, however salts with pharmaceutically acceptable acids are preferred; examples of such salts are amlodipine besylate, amlodipine maleate, amlodipine fumarate, amlodipine hydrochloride, amlodipine mesylate, etc. Typically such amlodipine products are made in batches or lots for production purposes. A production lot should be checked to insure that the level of any of amlodipine analogue (1b)–(1f) is within specification; i.e., a quality control test to insure that the amlodipine impurities (1b)–(1f) are below a predetermined limit. A sample from the production lot is taken and assayed for the presence of amlodipine analogue and preferably also for the content of amlodipine. Typically the production lot must contain less than 1.0 wt %, preferably less than 0.5%, more preferably less than 0.2% and most preferably less than 0.1% of any of the compounds (1b)–(1f) based on the amount of amlodipine or amlodipine salt. Generally the entire production lot, minus any retained sample(s), will be released by the manufacturer unless an unacceptable level of amlodipine impurity is found. In that case, the production lot will not be sold or released; i.e. neither placed in commerce nor used in production of final forms.

The amlodipine analogue (1b)–(1f) is assayed under a set of conditions to produce a reference standard analytical result. A "reference standard analytical result" may be a quantitative or qualitative result and can be in any form including numerical, graphical, pictorial, etc. In some cases the result can be stored electronically for later comparisons.

Assaying of the amlodipine product results in an analytical result for the sample. Typically the sample analytical result is compared in some fashion to the reference standard analytical result for corresponding amlodipine analogue. The comparison can be done manually such as by visual observation and/or by an automated procedure. The reference standard analytical results can be obtained essentially concurrently with the sample analytical results such as immediately before, during or immediately after the assaying of the amlodipine product sample, or they can be obtained earlier, even months or years earlier. In some embodiments the reference standard analytical results are electronically stored and used by a computer algorithm to determine the presence of the amlodipine analogue and its amount. This latter embodiment includes calibrating the equipment based on the reference standard analytical results or results derived therefrom and/or providing a so-called internal normalization. All such comparisons, whether direct, indirect, manual or automated, are included within the meaning of "comparing."

The assay used in determining the reference standard analytical results is generally also the same assay with the same set of conditions used to test the amlodipine product, although such is not necessarily required.

The invention will be further described with reference to the two preferred assay techniques, namely TLC and HPLC. In TLC, samples of the tested amlodipine product, and reference standards of amlodipine analogues are chromatographed on a suitable chromatographic plate by a suitable developing liquid (mobile phase) under set conditions. These conditions include the solvent, the concentration of the sample in the solvent and the amount of solution applied to the plate. Selecting appropriate solvents and concentrations is well known within the art. The analytical results produced under these conditions may include the $R_f$ value, namely the ratio of distance traveled by the corresponding material to the distance traveled by the solvent, and/or the size of the spot produced on the chromatogram.

Preferably, the reference standard is applied at the same time and to the same chromatographic plate as the tested sample thereby allowing for side-by-side comparisons. In other embodiments the reference standard is already defined and is simply compared with the developed sample chromatogram. Amlodipine analogues may also be premixed in defined ratios to form a mixed reference standard.

Thus one process for testing the purity of a sample comprising amlodipine comprises the steps of:

a) dissolving a sample comprising amlodipine in a solvent to produce a sample solution b) dissolving a sample of any or more of amlodipine analogues 1b)–1f) in a solvent to produce a reference solution c) subjecting the sample solution and the reference solution to thin layer chromatography to obtain a TLC chromatogram for each and d) estimating the intensity of any secondary spot obtained from the sample solution which corresponds in $R_f$ value to the reference marker, against the intensity of the spot due to the corresponding amlodipine analogue in the chromatogram of the reference solution.

Similarly an assay using HPLC can also be formulated. The reference standard analytical results may include the resolution factor, response factor, the retention time, and/or the peak area. For example, a process for testing the of a sample comprising amlodipine comprises the steps of:

a) dissolving a sample comprising amlodipine in a solvent to produce one or more sample solutions b) dissolving a sample of any or more of amlodipine analogues (1b)–(1f) in a solvent to produce a reference solution c) injecting the sample and reference solutions to an HPLC column and d) estimating the peak areas of each solution and calculating from these the content of the or any of the amlodipine analogue (s) (1b)–(1f) in each sample solution.

In this embodiment, it may be necessary or desirable to run a system suitability solution through the HPLC column prior to step c) in order to determine the resolution factor between amlodipine and any other compound present in the sample. In that case the method includes the additional step of b') dissolving amlodipine and a suitable external standard (s) to produce a system suitability solution, and injecting the system suitability solution onto the HPLC column to determine resolution factor(s).

As an alternative to assaying a sample of the reference marker separately each time, a parameter known as the Response factor (R) may be used. The response factor is a previously determined ratio of a numerical result (e.g. peak area at HPLC) obtained by testing a sample of the aspartate or the maleamide, by a given analytical technique, to the corresponding numerical result obtained by testing the same amount of pure amlodipine maleate at an equivalent concentration. The known response factor for amlodipine aspartate or amlodipine maleamide can be used to calculate the amount of that particular marker in the test sample. In this way, the relative amount of the impurity to the amlodipine maleate in the sample can be determined as is well known in the art.

The principles and techniques of testing of purity of amlodipine products disclosed above may be, mutatis mutandis, applied also for testing of purity of corresponding phthalimido-protected precursor products of formula (2) (e.g., raw, purified, reaction mixtures comprising the same, salts thereof, etc), using compounds (2a)–(2f) as reference markers. The testing of phthalimidoamlodipine products for the presence and amount of phthalimidoamlodipine impurities (2b)–(2f) is important as, knowing the corresponding result, a producer may properly decide whether and how the phthalimidoamlodipine product may be purified or otherwise reprocessed before its conversion to amlodipine and, accordingly, whether or how the conditions in production of phthalimidoamlodipine should be adjusted to obtain a product with improved quality. Phthalimidoamlodipine having the content of any of analogues (2b)–(2f) below a predetermined limit may yield amlodipine essentially free of the corresponding amlodipine impurities (1b)–(1f) so that the amlodipine is not required to be further purified; thus saving time and energy and improving the overall economy of the amlodipine production. Typically the impurity level should be less than 1 wt %, preferably less than 0.5 wt %, more preferably less than 0.2 wt % and even less than 0.1 wt %.

In one embodiment, a batch of phthalimidoamlodipine is tested for purity by removing a sample therefrom and assaying for one or more of the potential phthalimidoamlodipine impurities (2b)–(2f). The presence and amount of impurity are determined by comparison to a known reference standard analytical result for the impurity such as by HPLC or TLC as described above. If the sample is determined to contain the impurity below a predetermined level, then the phthalimidoamlodipine batch is subjected to a deprotection step to form a batch of amlodipine. If the sample is determined to contain an amount of the impurity above the predetermined level, then the phthalimidoamlodipine batch can be re-processed or purified such as by crystallization in order to reduce the impurity level below the predetermined limit, or it may be discarded. In this way, amlodipine product is not produced when the product will inevitably have too much amlodipine impurity. Not only can such a process improve efficiency and cut waste but also, in some circumstances, it may be easier to separate the phthalimidoamlodipine impurities from phthalimidoamlodipine than it is to separate the anilodipine impurities from amlodipine; thereby improving the overall yield. The batch of phthalimidoamlodipine from which a sample is taken can be either the crude or isolated phthalimidoamlodipine product or it can be a purified product. For example, a purified product can be obtained by (re)crystallizing the isolated product one or more times as described above. Other purification techniques can also be used, if desired. Generally the level of phthalimidoamlodipine impurity is set to 1.0 wt % or less, more typically 0.5 wt % or less, and even less than 0.1 wt %. Once the phthalimidoamlodipine batch is determined to contain the less than the predetermined amount of impurity, the batch is subjected to deprotection and converted to a batch of amlodipine. The amlodipine is generally converted to a pharmaceutically acceptable salt thereof and then combined with at least one pharmaceutically acceptable excipient to form a pharmaceutical unit dosage form such as a tablet or a capsule. These unit dosage forms contain an effective amount of amlodipine. Preferably, the amlodipine batch, or the amlodipine salt, or the amlodipine unit dosage form, or a combination thereof are subjected to an assay for the level of at least one amlodipine impurity of (1b)–(1f). If the level of amlodipine impurity is above a predetermined level, then the amlodipine product may be re-processed or otherwise not released or sold.

The following Examples illustrate the invention.

EXAMPLE 1

Ethyl 2-(o-chlorobenzylidene)-4-(2-phthalimidoethoxy)acetoacetate (Compound 3a)

300 g of ethyl 4-(2-(phthalimido)ethoxy)acetoacetate was mixed with 90 ml of 2-chlorobenzaldehyde and 140 ml of 2-propanol. The solution was agitated at 20–25° C. and the solution of 3.6 ml of piperidine in 40 ml of 2-propanol was added dropwise during 2 hours. The mixture was than stirred for 1 hour at the same temperature and 2 hours at 35–40° C. The mixture was acidified with 4.1 ml of acetic acid, 500 ml of 2-propanol was added and the solution was cooled to 0–5° C. Two layers are formed in the reaction mixture; the upper one was separated and the lower organic layer was again washed with 200 ml of 2-propanol. The organic layer, containing the desired product, was evaporated to dryness in order to remove the residual solvent.

Yield: 350 g (84%), as the mixture of cis and trans isomers (6:4). Content of 2-chlorobenzaldehyde less than 5%.

EXAMPLE 1A

Ethyl 2-(o-chlorobenzylidene)-4-(2-phthalimidoethoxy)acetoacetate (Compound 3a)

| | |
|---|---|
| 4.2 g | of ethyl 4-(2-(phthalimido)ethoxy)acetoacetate was dissolved in |
| 4 ml | of isopropanol, under $N_2$, at room temperature. |
| 1.9 g | of 2-chlorobenzaldehyde was added thereto. |
| 0.075 g | of piperidine in |
| 1 ml | of IPA was added slowly in 2 hours. When addition was complete the mixture was heated to 35°–40° C. for 2 hours. |
| 0.8 g | of acetic acid glacial in |
| 4 ml | of IPA was added and the mixture was cooled to 3°–5° C. in the refrigerator. The solvent was decanted and the gum like solid washed with |
| 2 × 5 ml | of IPA. |

For analytical purposes, a portion of the raw product was purified by a chromatography on silica gel 60 using a 1:1 (v/v) mixture of ethyl acetate and n-heptane as the eluent. After collection of the fraction containing the product, the solvent was evaporated leaving an oil.

NMR shows a mixture of Z and E-isomers, whereby the Z/E ratio is approximately 6:4.

$^1$H-NMR Spectrum:

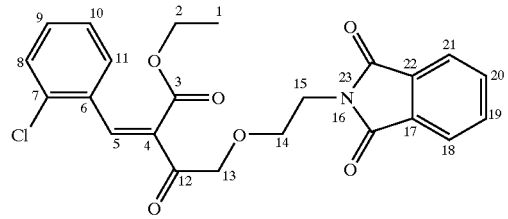

The $^1$H-NMR spectrum was measured at 303.2 K on a Bruker Avance-400 in deuterated chloroform at 400 MHz.

| δ | Assignment |
|---|---|
| 1.12 | (t, ~1.2H, $J_{1,2}$=7.2Hz, $H\text{-}1_{(E)}$); |
| 1.32 | (t, ~1.7H, $J_{1,2}$=7.2Hz, $H\text{-}1_{(Z)}$); |
| 3.70 | (t, ~1.2H, $J_{14,15}$=5.6Hz, $H\text{-}14_{(E)}$); |
| 3.81 | (t, ~0.8H, $J_{14,15}$=5.6HZ, $H\text{-}14_{(Z)}$); |
| 3.86 | (t, ~1.2H, $J_{14,15}$=5.6Hz, $H\text{-}15_{(E)}$); |
| 3.94 | (t, ~0.8H, $J_{14,15}$=5.6Hz, $H\text{-}15_{(Z)}$); |
| 4.17 | (s, $H\text{-}13_{(E)}$); |
| 4.18 | (q, $J_{1,2}$=7.2Hz, $H\text{-}2_{(Z)}$) (+4.17 sum 2H); |
| 4.27 | (q, ~1.2H, $J_{1,2}$=7.2Hz, $H\text{-}2_{(E)}$); |
| 4.48 | (s, ~0.7H, $H\text{-}13_{(Z)}$); |
| 7.26 | (bm, 3H, $H\text{-}9_{(E+Z)}$+$H\text{-}10_{(E+Z)}$+$H\text{-}11_{(E+Z)}$); |
| 7.40 | (bd, 1H, $H\text{-}8_{(E+Z)}$); |
| 7.70 | (m, ~2H, $H\text{-}19_{(E+Z)}$+$H\text{-}20_{(E+Z)}$); |
| 7.81 | (m, 2H, $H\text{-}18_{(E+Z)}$+$H\text{-}21_{(E+Z)}$); |
| 7.92 | (s, $H\text{-}5_{(Z)}$); |
| 7.94 | (s, $H\text{-}5_{(E)}$) (+7.92 sum ~1H). |

$^{13}$C-NMR Spectrum:

The $^{13}$C-NMR spectrum was measured at 303.2 K on a Bruker Avance-400 in deuterated chloroform at 100.6 MHz.

| δ | Assignment |
|---|---|
| 13.65 | (C-$1_{(Z)}$); |
| 14.04 | (C-$1_{(E)}$); |
| 37.13 | (C-$15_{(E)}$); |
| 37.19 | (C-$15_{(Z)}$); |
| 61.53 | (C-$2_{(Z)}$); |
| 61.71 | (C-$2_{(E)}$); |
| 68.21 | (C-$14_{(Z)}$); |
| 68.39 | (C-$14_{(E)}$); |
| 74.20 | (C-$13_{(Z)}$); |
| 75.69 | (C-$13_{(E)}$); |
| 123.13 | (C-$18_{(E)}$+C-$21_{(E)}$); |
| 123.17 | (C-$18_{(Z)}$+C-$21_{(Z)}$); |
| 126.52 | (C-$11_{(Z)}$); |
| 127.02 | (C-$11_{(E)}$); |
| 129.56 | (C-$8_{(Z)}$); |
| 129.65 | (C-$10_{(Z)}$); |
| 129.81 | (C-$8_{(E)}$); |
| 130.13 | (C-$10_{(E)}$); |
| 131.09 | (C-$9_{(Z)}$); |
| 131.20 | (C-$9_{(E)}$); |
| 131.57 | (C-$6_{(E)}$); |
| 132.08 | (C-$17_{(E+Z)}$+C-$22_{(E+Z)}$); |
| 132.29 | (C-$6_{(Z)}$); |
| 133.64 | (C-$4_{(Z)}$); |
| unknown | (C-$4_{(E)}$); |
| 133.81 | (C-$19_{(Z)}$+C-$20_{(Z)}$); |
| 133.83 | (C-$19_{(E)}$+C-$20_{(E)}$); |
| 134.50 | (C$7_{(E)}$); |
| 134.60 | (C-$7_{(Z)}$); |
| 139.93 | (C-$5_{(E)}$); |
| 140.18 | (C-$5_{(Z)}$); |
| 163.65 | (C-$3_{(E)}$); |
| 165.95 | (C-$3_{(Z)}$); |
| 168.04 | (C-$16_{(E)}$+C-$23_{(E)}$); |
| 168.09 | (C-$16_{(Z)}$+C-$23_{(Z)}$); |
| 194.15 | (C-$12_{(Z)}$); |
| 201.53 | (C-$12_{(E)}$). |

EXAMPLE 2

3-Ethyl 5-methyl 4-(2-chlorophenyl)-2-{[2-(1.3-dioxo-1.3-dihydro-2H-isoindol-2-yl)ethoxy]methyl}-6-methyl-1.4-dihydro-3.5-pyridine dicarboxylate (= phthalimidoamlodipine, Compound 2a)

350 g of crude ethyl 2-(o-chlorobenzylidene)-4-(2-phthalimidoethoxy) acetoacetate from Example 1 was dissolved in 540 ml of 2-propanol at 80° C. 50 g of methyl-3-aminocrotonate was added and the mixture was heated at the same temperature for 16 hours. The mixture was evaporated to dryness. The residue was dissolved in 540 ml of glacial acetic acid at 80° C. The mixture was cooled to 15° C. and stirred at the same temperature for 20 hours. The formed solid was filtered off and washed with 280 ml of glacial acetic acid. The solid was suspended in 225 ml of methanol and agitated for 30 minutes. The solid was filtered off, washed with 75 ml of methanol and dried.

Yield: 229.5 g (56%) of crude product, purity (HPLC) –98%

The product was recrystallized from ethyl acetate

Yield of the crystallisation: 90%, purity (HPLC) –99%.

EXAMPLE 3

Preparation of Amlodipine Maleate

Into a glass vessel, 80 ml of 40% aqueous methylamine and 8.0 g of the product from Example 2 were charged under stirring. The suspension was agitated at 25° C. for 24 hours. To the mixture, 120 ml of toluene was added and the mixture was agitated for 30 minutes. Then the agitation was stopped for separation of layers. The water layer was separated and discharged. The toluene layer was washed with 40 ml of water and toluene was evaporated at max. 60° C. on a rotary vacuum evaporator, until the first precipitate occurred. 4 ml of EtOH was added and after dissolving, the solution was filtered.

A solution of 1.74 g of maleic acid in 20 ml of EtOH was added to the ethanolic solution. After about 10 minutes of agitation, the solution started to crystallise. The mixture was cooled to 5–10° C. and agitated at the same temperature for 1 hour. The precipitate was filtered and washed with 2×6 ml of EtOH.

The product was dried at max 40° C. for 24 hours.

Yield: 5.84 g of amlodipine maleate.

EXAMPLE 4

Methyl 2-(o-chlorobenzylidene)-4-(2-phthalimidoethoxy)acetoacetate (Compound 3b)

85 g of methyl 4-(2-(phthalimido)ethoxy)acetoacetate was agitated with 31.7 ml of 2-chlorobenzaldehyde and 37 ml of 2-propanol at 20-25° C. The solution of 1.1 ml of piperidine in 14 ml of 2-propanol was added dropwise during 1.5 hour. The mixture was than agitated for 2 hours at the same temperature and for 2 hours at 35–40° C. The mixture was acidified with 1.5 ml of acetic acid, 140 ml of 2-propanol was added and the solution was cooled to 0–5° C. The isopropanolic layer was separated and the organic layer was again washed with 53 ml of 2-propanol. The organic layer, containing the desired product, was evaporated to dryness in order to remove the residual solvent.

Yield: 104 g (87%), as the mixture of cis and trans isomers.

EXAMPLE 5

Dimethyl 4-(2-chlorophenyl)-2-{[2-(1.3-dioxo-1.3-dihydro-2H-isoindol-2-yl)ethoxy]methyl}-6-methyl-1.4-dihydro-3.5-pyridine dicarboxylate (Compound 2c)

92.1 g of methyl 2-(o-chlorobenzylidene)-4-(2-phthalimidoethoxy)acetoacetate was dissolved in 108 ml of 2-propanol at 80° C. 31.3 g of methyl-3-aminocrotonate was added and the mixture was heated at the same temperature for 24 hours. The mixture was evaporated to dryness. The residue was dissolved in 162 ml of glacial acetic acid at 80° C. The mixture was cooled to 15° C. and stirred at the same temperature for 20 hours. The solid was filtered off and washed with 83 ml of glacial acetic acid. The solid was suspended in 68 ml of methanol and agitated for 30 minutes. The solid was filtered off, washed with 23 ml of methanol and dried. The product was recrystallized from ethyl acetate.

Yield: 77.7 g; 69%; purity (HPLC, IN) –96.8%; m.p. 197.5–199° C.

EXAMPLE 6

Diethyl 4-(2-chlorophenyl)-2-{[2-(1,3-dioxo-1.3-dihydro-2H-isoindol-2-yl)ethoxy]methyl}-6-methyl-1.4-dihydro-3.5-pyridine dicarboxylate (Compound 2b)

116.7 g of ethyl 2-(o-chlorobenzylidene)-4-(2-phthalimidoethoxy)acetoacetate was dissolved in 120 ml of 2-propanol at 80° C. 31.2 g of ethyl-3-aminocrotonate was added and the mixture was heated at the same temperature for 16 hours. The mixture was evaporated to dryness. The residue was dissolved in 180 ml of glacial acetic acid at 80° C. The mixture was cooled to 15° C. and stirred at the same temperature for 20 hours. The solid was filtered off and washed with 92 ml of glacial acetic acid. The solid was dissolved in 75 ml of ethanol at 80° C. The solution was cooled to 20° C. and the suspension was agitated for 2 h. The solid was filtered off, washed with 25 ml of ethanol. The wet product was recrystallized from 60 ml of ethyl acetate.

Yield: 43.6 g (30%) of the product, purity (HPLC, IN) –98.4%; m.p. 142.5–144° C.

EXAMPLE 7

3-Methyl 5-ethyl 4-(2-chlorophenyl)-2-{[2-(1.3-dioxo-1.3-dihydro-2H-isoindol-2-yl)ethoxy]methyl}-6-methyl-1.4-dihydro-3.5-pyridine dicarboxylate (Compound 2d)

87 g of methyl 2-(o-chlorobenzylidene)-4-(2-phthalimidoethoxy)acetoacetate was dissolved in 102 ml of 2-propanol at 80° C. 33.1 g of ethyl-3-aminocrotonate was added and the mixture was heated at the same temperature for 16 hours. The mixture was evaporated to dryness. The residue was dissolved in 153 ml of glacial acetic acid at 80° C. The mixture was cooled to 15° C. and stirred at the same temperature for 20 hours. The solid was filtered off and washed with 78 ml of glacial acetic acid. The solid was suspended in 150 ml of methanol and agitated at 60° C. for 30 minutes. The solid was cooled to 20° C. and filtered off, washed with 30 ml of methanol and dried. The product was recrystallized from ethyl acetate.

Yield: 80 g; 52%; purity (HPLC, IN) –98.2%; m.p. 158–160° C.

EXAMPLE 8

Synthesis of Dimethylamlodipine (Compound 1c) Maleate 62,48 g of compound 2c) was suspended in 630 ml of 40% solution of methylamine in water. Temperature of the mixture was adjusted at 25–26° C. and it was agitated for 24 hours. Then the mixture was extracted with 940 ml of toluene. Toluene layer was extracted with 310 ml of water. Toluene was distilled off at max. 60° C. on the water bath. The residue was dissolved in 70 ml of ethanol and 13,95 g of maleic acid in 270 ml of ethanol was added at ambient temperature. After several minutes of stirring, the solid started to precipitate. The mixture was stirred for 2 h at ambient temperature. The crystals were filtered off and washed with 2×50 ml of ethanol The solid was dried at 25° C. for 1 day.

Yield: 38.56 g (63.4% of theory).

Properties: crystalline compound—m.p. 165–166° C. from EtOH
¹H-NMR Spectrum:

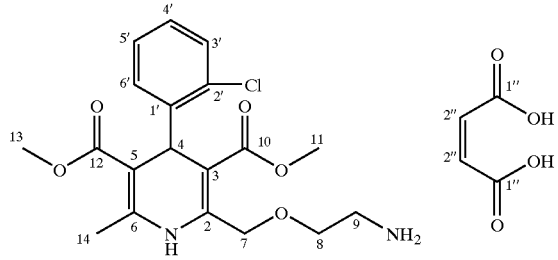

The ¹H-NMR spectrum was measured at 303.2 K on a Bruker Avance-400 in deuterated dimethylsulfoxide at 400 MHz.

| δ | Assignment |
|---|---|
| 2.34 | (s, 3H, H-14); |
| 3.12 | (bdd, 2H, H-9); |
| 3.52, 3.54 | (s+s, 3H+3H, H-11, H-13); |
| 3.68 | (m, 2H, H-8); |
| 4.65 | (ABq, 2H, H-7); |
| 5.34 | (s, 1H, H-4); |
| 6.08 | (s, 2H, H-2''); |
| 7.14 | (m, 1H, H-4'); |
| 7.24 | (bdt, 1H, H-5'); |
| 7.29 | (dd, 1H, $J_{3',5'}$=1.3Hz, $J_{3',4'}$=7.8Hz, H-3'); |
| 7.35 | (dd, 1H, $J_{4',6'}$=1.8Hz, $J_{5',6'}$=7.8Hz, H-6'); |
| 7.89 | (bs, ~3H+ |
| 8.45 | s, 1H, NH+HN$_2$+OH). |

¹³C-NMR Spectrum:
The ¹³C-NMR spectrum was measured at 303.2 K on a Bruker Avance-400 in deuterated dimethylsulfoxide at 100.6 MHz.

| δ | Assignment |
|---|---|
| 18.16 | (C-14); |
| 36.62 | (C-4); |
| 38.54 | (C-9); |
| 50.42, 50.65 | (C-11, C-13); |
| 66.51 | (C-7, C-8); |
| 102.00, 102.03 | (C-3, C-5); |
| 127.36 | (C-5'); |
| 127.71 | (C-4'); |
| 128.95 | (C-3'); |
| 130.74 | (C-6'); |
| 131.08 | (C-2'); |
| 135.84 | (C-2''); |
| 144.39 | (C-2); |
| 145.18 | (C-6); |
| 145.62 | (C-1'); |
| 166.63 | (C-10); |
| 167.00 | (C-12); |
| 167.24 | (C-1''). |

EXAMPLE 9

Synthesis of Diethylamlodipine (Compound 1b) Maleate

The compound was synthesized according to the same procedure as in Example 8, but starting from crystalline compound 2b ) (purity—98.4%).

Yield: 22.89 g (93.7% of theory)

Properties: crystalline compound—m.p. 179–180° C. from EtOH.
¹H-NMR Spectrum:

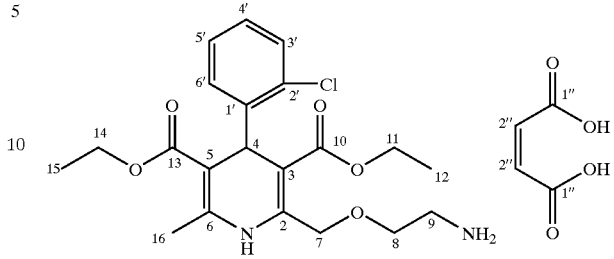

The ¹H-NMR spectrum was measured at 303.2 K on a Bruker Avance-400 in deuterated dimethylsulfoxide at 400 MHz.

| δ | Assignment |
|---|---|
| 1.12 | (t, J=7.0Hz+ |
| 1.13 | t, J=7.0Hz, sum 6H, H-12+H-15); |
| 2.33 | (s, 3H, H-16); |
| 3.11 | (dd, ~2H, J=4.3Hz, J=5.8Hz, H-9); |
| 3.68 | (m, 2H, H-8); |
| 4.00 | (m, 4H, H-11+H-14); |
| 4.65 | (ABq, 2H, H-7); |
| 5.33 | (s, 1H, H-4); |
| 6.08 | (s, 2H, 2×H-2''); |
| 7.15 | (m, 1H, H-4'); |
| 7.24 | (dt, 1H, $J_{3',5'}$=1.3Hz, $J_{5',6'}$=7.8Hz, H-5'); |
| 7.29 | (dd, 1H, $J_{3',5'}$=1.3Hz, $J_{3',4'}$=7.8Hz, H-3'); |
| 7.36 | (dd, 1H, $J_{4',6'}$=1.8Hz, $J_{5',6'}$=7.8Hz, H-6'); |
| 7.90 | (bs, ~3H+ |
| 8.38 | s, 1H, NH+NH$_2$+OH). |

¹³C-NMR Spectrum:
The ¹³C-NMR spectrum was measured at 303.2 K on a Bruker Avance-400 in deuterated dimethylsulfoxide at 100.6 MHz.

| δ | Assignment |
|---|---|
| 13.96, 14.02 | (C-12, C-15); |
| 18.27 | (C-16); |
| 36.87 | (C-4); |
| 38.55 | (C-9); |
| 59.00, 59.29 | (C-11, C-14); |
| 66.51, 66.61 | (C-7, C-8); |
| 102.07, 102.09 | (C-3, C-5); |
| 127.17 | (C-5'); |
| 127.69 | (C-4'); |
| 128.90 | (C-3'); |
| 131.09 | (C-6'); |
| 131.17 | (C-2'); |
| 135.97 | (2×C-2''); |
| 144.22 | (C-2); |
| 144.91 | (C-6); |
| 145.46 | (C-1'); |
| 166.25, 166.60 | (C-10, C-13); |
| 167.25 | (2×C-1''). |

EXAMPLE 10

Synthesis of Ethylmethylamlodipine (Compound 1d) Maleate

The compound was synthesized according to the same procedure as in Example 8, but starting from crystalline compound 2d) (purity—98.2%) and using methanol as a solvent for final precipitation.

Yield: 45.23 g (71.4% of theory)

Properties: crystalline compound—m.p. 188–189° C. from MeOH

¹H-NMR Spectrum:

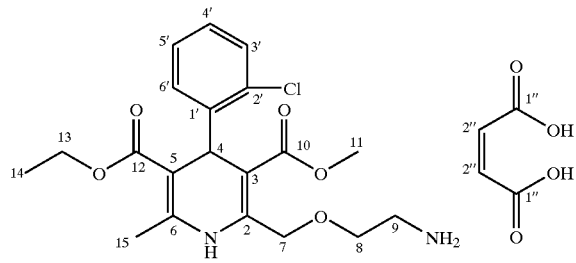

The ¹H-NMR spectrum was measured at 303.2 K on a Bruker Avance-400 in deuterated dimethylsulfoxide at 400 MHz.

| δ | Assignment |
|---|---|
| 1.11 | (t, 3H, $J_{13,14}$=7.0Hz, H-14); |
| 2.34 | (s, 3H, H-15); |
| 3.11 | (bdd, 2H, H-9); |
| 3.54 | (s, 3H, H-11); |
| 3.68 | (bt, 2H, H-8); |
| 3.99 | (q, 2H, $J_{13,14}$=7.0Hz, H-13); |
| 4.64 | (ABq, 2H, H-7); |
| 5.34 | (s, 1H, H-4); |
| 6.08 | (s, 2H, H-2"); |
| 7.14 | (dt, 1H, $J_{4',6'}$=1.8Hz, $J_{3',4'}$=7.8Hz, H-4'); |
| 7.24 | (bdt, 1H, H-5'); |
| 7.29 | (dd, 1H, $J_{3',5'}$=1.3Hz, $J_{3',4'}$=7.8Hz, H-3'); |
| 7.36 | (dd, 1H, $J_{4',6'}$=1.8Hz, $J_{5',6'}$=7.6Hz, H-6'); |
| 7.90 | (bs, ~3H+ |
| 8.41 | s, 1H, NH+NH$_2$+OH). |

¹³C-NMR Spectrum:

The ¹³C-NMR spectrum was measured at 303.2 K on a Bruker Avance-400 in deuterated dimethylsulfoxide at 100.6 MHz.

| δ | Assignment |
|---|---|
| 14.02 | (C-14); |
| 18.24 | (C-15); |
| 36.72 | (C-4); |
| 38.54 | (C-9); |
| 50.63 | (C-11); |
| 58.98 | (C-13); |
| 66.50, 66.52 | (C-7, C-8); |
| 101.96 | (C-3); |
| 102.20 | (C-5); |
| 127.28 | (C-5'); |
| 127.70 | (C-4'); |
| 128.92 | (C-3'); |
| 130.90 | (C-6'); |
| 131.12 | (C-2'); |
| 135.94 | (C-2"); |
| 144.26 | (C-2); |
| 145.08 | (C-6); |
| 145.58 | (C-1'); |
| 166.54 | (C-12); |
| 166.68 | (C-10); |
| 167.24 | (C-1"). |

EXAMPLE 11

3-Ethyl 5-prop-2-yl 4-(2-chlorophenyl)-2-{[2-(1.3-dioxo-1.3-dihydro-2H-isoindol-2-yl)ethoxy]methyl}-6-methyl-1,4-dihydro-3,5-pyridine dicarboxylate (Compound 2e)

15 g of phthalimidoamlodipine (2a) was suspended in 150 ml of 2-propanol. To this suspension was added 0.5 ml of concentrated sulfuric acid and the mixture was heated to reflux and for 72 hours. The mixture was cooled to room temperature and partially evaporated. 50 ml of n-heptane was added under stirring. A solid started to form, which was filtered off and washed with 25 ml of n-heptane. The obtained solid was dissolved in ethyl acetate for crystallization, but no crystals were formed even after addition of n-heptane, oil. The mixture was evaporated and the residual solid dissolved in 35 ml of 2-propanol at reflux. During cooling a solid started to form. The solid was filtered off and washed with 10 ml of 2-propanol. After drying at 40° C. under vacuum, 10 g of a yellow solid was obtained.

Purity: 90% (HPLC) of the title compound.

¹H-NMR Spectrum:

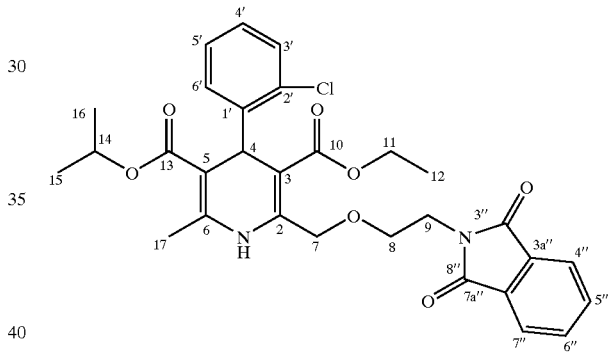

The ¹H-NMR spectrum was measured at 303.2 K on a Bruker Avance-400 in deuterated chloroform at 400 MHz.

| δ | Assignment |
|---|---|
| 1.04 | (d, 3H, $J_{14,15}$=6.3Hz, H-15); |
| 1.16 | (t, $J_{11,12}$=7.0Hz, H-12) |
| 1.24 | (d, $J_{14,16}$=6.3Hz, H-16); |
| 2.42 | (s, 3H, H-17); |
| 3.76 | (m, 2H, H-8); |
| 4.02 | (m, ~4H, H-11+H-9); |
| 4.66 | (ABq, 2H, H-7); |
| 4.97 | (septet, 1H, $J_{14,15}$=$J_{14,16}$=6.3Hz, H-14); |
| 5.35 | (s, 1H, H-4); |
| 7.00 | (bdt, 1H, $J_{4',6'}$=1.8Hz, J~7.7Hz, H-4'); |
| 7.08 | (dt, 1H, $J_{3',5'}$=$J_{4',5'}$=1.5Hz, $J_{5',6'}$=7.5Hz, H-5'); |
| 7.19 | (dd, 1H, $J_{3',5'}$=1.5Hz, $J_{3',4'}$=7.8Hz, H-3'); |
| 7.31 | (bs, NH) |
| 7.35 | (dd, $J_{4',6'}$=1.8Hz, $J_{5',6'}$=7.5Hz, H-6') (+7.31 sum 2H); |
| 7.76 | (m, 2H, H-5"+H-6"); |
| 7.88 | (m, 2H, H-4"+H-7"). |

¹³C-NMR Spectrum:

The ¹³C-NMR spectrum was measured at 303.2 K on a Bruker Avance-400 in deuterated chloroform at 100.6 MHz.

| δ | Assignment |
|---|---|
| 14.23 | (C-12); |
| 18.94 | (C-17); |
| 21.54, 21.89 | (C-15, C-16); |
| 37.29 | (C-4); |
| 37.95 | (C-9); |
| 59.57 | (C-11); |
| 66.83 | (C-14); |
| 68.18 | (C-7); |
| 68.94 | (C-8); |
| 100.63 | (C-3); |
| 104.16 | (C-5); |
| 123.35 | (C-4", C-7"); |
| 126.54 | (C-5'); |
| 127.16 | (C-4'); |
| 129.10 | (C-3'); |
| 131.78 | (C-6'); |
| 132.00 | (C-3a", C-7a"); |
| 132.34 | (C-2'); |
| 134.18 | (C-5", C-6"); |
| 144.10 | (C-6); |
| 144.90 | (C-2); |
| 145.69 | (C-1'); |
| 167.15 | (C-13); |
| 167.17 | (C-10); |
| 168.48 | (C-3", C-8"). |

EXAMPLE 12

5-methyl 3-prop-2-yl 4-(2-chlorophenyl)-2-{[2-(1.3-dioxo-1.3-dihydro-2H-isoindol-2-yl)ethoxy]methyl}-6-methyl-1.4-dihydro-3,5-pyridinedicarboxylate (Compound 2f)

Step 1): Isopropyl 2-(o-chlorobenzylidene)-4-(2-phthalimidoethoxy)-acetoacetate (Compound 3c)

17 g of isopropyl 4-(2-(phthalimido)ethoxy)acetoacetate was dissolved in 15 ml of isopropanol, under N2, at room temperature, and 7.5 g of 2-chlorobenzaldehyde was added. A solution of 0.25 g of piperidine in 5 ml of isopropanol was added slowly in 2 hours. When addition was complete, the mixture was heated to 35°–40° C. and kept there for 2 hours. 1.5 g of glacial acetic acid was added and the mixture was put at −20° C. The solvent was decanted and the remaining solid dissolved in 10 ml of isopropanol and put at −20° C. The solvent was decanted again to yield an oil.

For analytical purposes, 5 g of the remaining oil was purified by chromatography on silica gel using ethyl acetate/n-heptane 1/1 (v:v) mixture as the eluent.

Step 2) Condensation with Methyl 3-aminocrotonate 20 g of the oil prepared according to Step 1 was dissolved in 30 ml of isopropanol and 5.1 g of methyl 3-aminocrotonate was added under nitrogen. The mixture was heated to reflux for 18 hours under stirring. The mixture was cooled to room temperature and evaporated to dryness. 15 ml of glacial acetic acid was added. A solid was formed which was filtered off and washed with 5 ml of glacial acetic acid. The crude product was recrystallized from 25 ml of ethyl acetate. After drying at 50° C. under vacuum, 10.2 g of a slightly yellow solid was obtained. The solid was recrystallized from ethyl acetate leaving 9.8 g of a solid.

$^1$H-NMR Spectrum

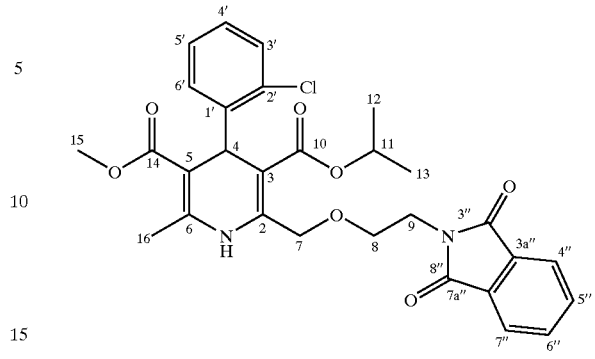

The $^1$H-NMR spectrum was measured at 303.2 K on a Bruker Avance-400 in deuterated chloroform at 400 MHz.

| δ | assignment |
|---|---|
| 0.98 | (d, 3H, $J_{11,12}$=6.3Hz, H-12); |
| 1.23 | (d, ~3H, $J_{11,13}$=6.3Hz, H-13); |
| 2.41 | (s, ~3H, H-16); |
| 3.61 | (s, ~3H, H-15); |
| 3.77 | (m, ~2H, H-8); |
| 4.01 | (m, ~2H, H-9); |
| 4.69 | (ABq, ~2H, H-7); |
| 5.34 | (s, 1H, H-4); |
| 7.01 | (m, 1H, H-4'); |
| 7.08 | (dt, 1H, $J_{3',5'}$=1.5Hz, $J_{5',6'}$=7.5Hz, H-5'); |
| 7.19 | (dd, 1H, $J_{3',5'}$=1.5Hz, $J_{3',4'}$=7.8Hz, H-3'); |
| 7.33 | (bs, NH)+ |
| 7.34 | (dd, $J_{4',6'}$=1.8Hz, $J_{5',6'}$=7.5Hz, H-6') (+7.33 sum~2H); |
| 7.76 | (m, 2H, H-5"+H-6"); |
| 7.88 | (m, 2H, H-4"+H-7"). |

$^{13}$C-NMR Spectrum:

The $^{13}$C-NMR spectrum was measured at 303.2 K on a Bruker Avance-400 in deuterated chloroform at 100.6 MHz.

| δ | Assignment |
|---|---|
| 18.89 | (C-16); |
| 21.45, 21.86 | (C-12, C-13); |
| 37.08 | (C-4); |
| 37.97 | (C-9); |
| 50.61 | (C-15); |
| 66.97 | (C-11); |
| 68.22 | (C-7); |
| 68.95 | (C-8); |
| 101.33 | (C-3); |
| 103.57 | (C-5); |
| 123.37 | (C-4", C-7"); |
| 126.69 | (C-5'); |
| 127.16 | (C-4'); |
| 129.06 | (C-3'); |
| 131.57 | (C-6'); |
| 131.99 | (C-3a", C-7a"); |
| 132.26 | (C-2'); |
| 134.20 | (C-5", C-6"); |
| 144.44 | (C-6); |
| 144.89 | (C-2); |
| 145.90 | (C-1'); |
| 166.65 | (C-10); |
| 168.13 | (C-14); |
| 168.51 | (C-3", C-8"). |

The invention having been described, it will be readily apparent to those skilled in the art that further changes and modifications in actual implementation of the concepts and

We claim:
1. A compound having the formula (3):

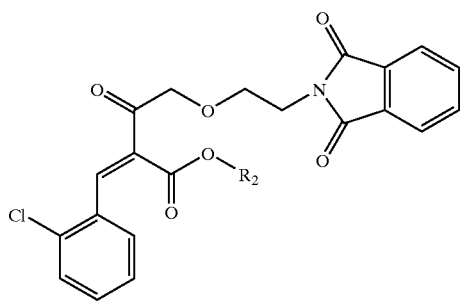

(3)

wherein $R_2$ is a $C_1$–$C_4$ alkyl group.

2. The compound according to claim 1, wherein said compound is in isolated form.

3. The compound according to claim 1 in the form of an oil.

4. The compound according to claim 1, wherein said compound is in the form of a mixture of cis and trans isomers.

5. The compound according to claim 1, wherein $R_2$ is a methyl group, an ethyl group, or an isopropyl group.

6. The compound according to claim 4, wherein $R_2$ is an ethyl group.

7. The compound according to claim 5, wherein said compound is in the form of a mixture of cis and trans isomers.

8. The compound according to claim 5, in the form of an oil.

* * * * *